United States Patent [19]

Rubenstein

[11] Patent Number: 5,755,664
[45] Date of Patent: May 26, 1998

[54] WAVEFRONT DIRECTION MAPPING CATHETER SYSTEM

[75] Inventor: Donald S. Rubenstein, Lombard, Ill.

[73] Assignee: Arch Development Corporation, Chicago, Ill.

[21] Appl. No.: 678,163

[22] Filed: Jul. 11, 1996

[51] Int. Cl.⁶ ............ A61B 5/04; A61B 5/0402; A61N 1/05

[52] U.S. Cl. ............ 600/377; 607/122; 607/125; 607/8

[58] Field of Search ............ 128/642, 696, 128/695; 607/8, 122, 125; 600/374, 377, 508, 509

[56] References Cited

U.S. PATENT DOCUMENTS

| | | | |
|---|---|---|---|
| 4,532,924 | 8/1985 | Auth et al. | 128/303.17 |
| 4,848,352 | 7/1989 | Pohndorf et al. | 128/642 |
| 5,158,092 | 10/1992 | Glace | 128/705 |
| 5,215,103 | 6/1993 | Desai | 128/784 |
| 5,231,995 | 8/1993 | Desai | 128/784 |
| 5,324,284 | 6/1994 | Imran | 607/122 |
| 5,365,926 | 11/1994 | Desai | 128/642 |
| 5,383,917 | 1/1995 | Desai et al. | 607/702 |
| 5,397,339 | 3/1995 | Desai | 607/116 |
| 5,399,164 | 3/1995 | Snoke et al. | 604/95 |
| 5,419,767 | 5/1995 | Eggers et al. | 604/114 |
| 5,427,112 | 6/1995 | Noren et al. | 128/702 |
| 5,433,198 | 7/1995 | Desai | 128/642 |
| 5,462,545 | 10/1995 | Wang et al. | 606/41 |
| 5,476,495 | 12/1995 | Kordis et al. | 607/122 |
| 5,482,037 | 1/1996 | Borghi | 607/122 |
| 5,637,090 | 6/1997 | McGee et al. | |

FOREIGN PATENT DOCUMENTS

| | | | |
|---|---|---|---|
| 571797 | 12/1993 | WIPO | 607/122 |
| 9415528 | 7/1994 | WIPO | 128/642 |

*Primary Examiner*—William E. Kamm
*Assistant Examiner*—Carl H. Layno
*Attorney, Agent, or Firm*—Rockey, Milnamow & Katz, Ltd.

[57] ABSTRACT

A wavefront direction mapping catheter system is disclosed which includes a wire catheter that, when placed on the inner surface of the heart, identifies the direction of the electric field wavefront, and provides output signals for indicating the manner in which a position controller of the system is to be operated for moving the distal tip portion of the catheter toward the source of the wavefront. The distal tip portion of the catheter includes a bipolar electrode array, preferably including first and second pairs of orthogonally arranged bipolar electrodes which provide signals to an analyzer of the system, whereby vector analysis of the wavefront is performed. The signal analysis permits the catheter to be moved toward and positioned at the source of the wavefront or within the wavefront circuit, with the present system thereafter being configured to effect radio frequency energization of the bipolar electrode array for tissue ablation.

16 Claims, 2 Drawing Sheets

WAVEFRONT DIRECTION MAPPING CATHETER SYSTEM

TECHNICAL FIELD

The present invention relates generally to systems for electrophysiologic study of cardiac electrical wavefronts, and more particularly to a wavefront direction mapping system which includes an internally positionable catheter system having a bipolar electrode array, with associated analysis and control means provided for selectively directing the catheter in the direction of the wavefront, and for effecting application of a radio frequency ablation lesion.

BACKGROUND OF THE INVENTION

The heart is provided with a special system for generating rhythmical impulses to cause rhythmical contraction of the heart muscle, and for conducting these impulses rapidly throughout the heart. When this system functions normally, the atria contract about one-sixth of a second ahead of ventricular contraction, which allows extra filling of the ventricles before they pump the blood through the lungs and peripheral circulation. Of special importance is that this system allows all portions of the ventricles to contract almost simultaneously, which is essential for effective pressure generation in the ventricular chambers.

The electrical impulse traveling through the heart is generally referred to as the activation wavefront, the direction of which is critical to proper heart function. Irregularities in the rhythmic function of the heart (arrhythmias), if of sufficient severity, can be life-threatening.

Treatment of such arrhythmias typically entails electrophysiologic study of the electrical wavefront, determination of its direction, and selective ablation of tissue such as by the application of a radio frequency ablation lesion. The present invention is directed to a system for mapping the wavefront, that is, determining its direction, with subsequent application of radio frequency energy for tissue ablation.

SUMMARY OF THE INVENTION

The present invention is directed to a wavefront direction mapping catheter system which includes a cardiac wire catheter that, when placed on the inner surface of the heart, identifies the direction of the electric field wavefront by analysis of signals received from the catheter by an on-line computer of the system. Significantly, the catheter is configured to include a bipolar electrode array mounted on a distal tip portion of the catheter, which tip portion is selectively rotationally positionable with respect to a body portion of the catheter. Output signals are generated by the computer of this system, whereby the catheter, including the distal tip portion thereof, can be selectively positioned and directed toward the source of the wavefront. The system can then be operated to apply radio frequency energy for ablation of tissue.

Thus, the present system is operable to determine the locus or circuit of wavefront generation, with the repeated steps of signal analysis, and movement of the bipolar electrode array in response thereto, effecting positioning of the electrode array at the source of the wavefront or within the wavefront circuit. Tissue ablation can then be effected by selective energization of the electrode array.

In accordance with the illustrated embodiment, the present system includes a catheter configured for positioning internally of a patient's heart. The catheter includes a generally elongated catheter body defining a longitudinal axis, and a distal tip portion movably mounted on a distal end of the catheter body.

The tip portion of the catheter includes a bipolar electrode array which includes at least one pair of bipolar electrodes for contact with the patient's heart for providing signals in response to a wavefront moving through the heart. In the preferred form, at least two orthogonally oriented pairs of bipolar electrodes are provided. In a presently, most preferred form in accordance with the illustrated embodiment, a generally spherically shaped distal tip portion is provided, with the electrode array including a pair of axially spaced electrodes respectively positioned in each of the quadrants of the spherically shaped distal tip portion.

An electrically conductive connector is provided joined to the bipolar electrode array, with the connector extending from the patient for providing signals from the array. An arrangement for signal analysis, in the form of an on-line computer, analyzes signals received from the electrode array via the connector. The computer of this system is configured to analyze the direction of the wavefront, and provide an output signal for directing the catheter toward the source of the wavefront.

The system further includes a position control arrangement which is operatively connected to the catheter for selectively positioning the distal tip portion thereof relative to the catheter body about a rotational axis. The distal tip portion of the catheter is positioned in response to the output signal of the system computer for mapping the direction of the wavefront.

It is presently preferred that wavefront mapping, by vector analysis, be effected three-dimensionally, and accordingly, selective positioning of the bipolar electrode array with respect to x, y, and z axes is preferred. To this end, the distal tip portion of the catheter is rotationally positionable with respect to the body of the catheter about a first rotational axis (the x-axis) which is perpendicular to the longitudinal axis of the catheter body. The distal tip portion of the catheter is further rotationally positionable about a second axis (the y-axis) which is perpendicular to the first rotational axis. Y-axis positioning can be effected by rotational movement of the distal tip portion, relative to the catheter body, about a second axis which is perpendicular to the longitudinal axis of the body. Alternatively, the distal tip portion of the catheter, either separately from or together with the catheter body, is rotatable about a second rotational axis which is coaxial with the longitudinal axis of the catheter body (such as by "torquing" of the catheter). As will be appreciated, z-axis movement of the electrode array mounted on the distal tip portion of the catheter is effected by displacement of the catheter along the longitudinal axis of the catheter body.

In the preferred form of the present system, the system includes an indicator arrangement for providing visual indication of the manner in which the position controller of the system is to be operated for positioning the distal tip portion of the catheter in the direction of the wavefront. The indicator arrangement is preferably configured to provide for selective positioning of the distal tip portion (and the bipolar electrode array carried thereby) with respect to the x-axis, the y-axis, and the z-axis.

Upon mapping of the electrical wavefront, and selective positioning of the catheter in the direction of the wavefront, the present system can be operated for energization of the electrode array for tissue ablation by application of a radio frequency ablation lesion.

Other features and advantages of the present invention will become readily apparent from the following detailed description, the accompanying drawings, and the appended claims.

DETAILED DESCRIPTION

Figure 1:
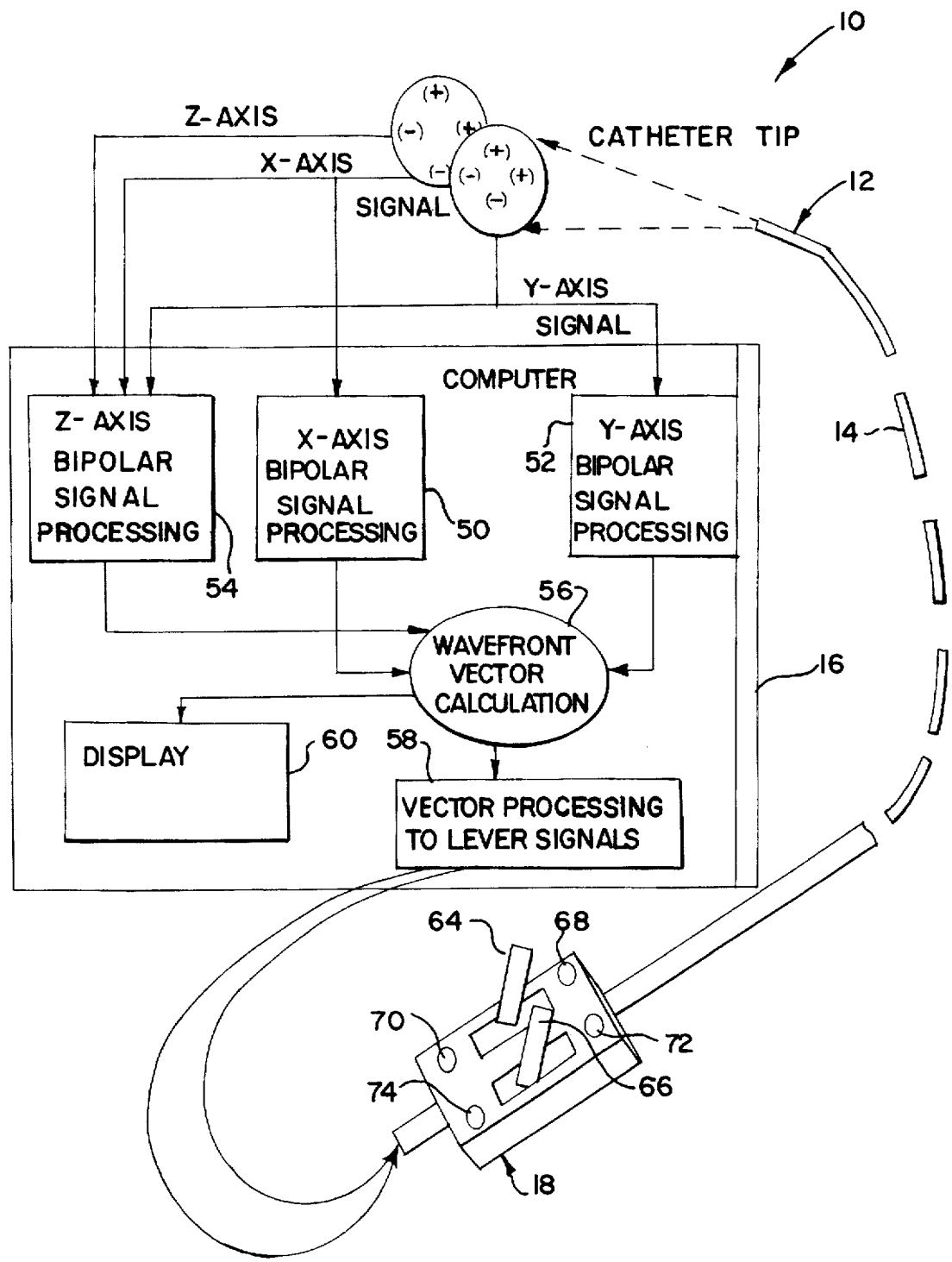
FIG. 1 is a diagrammatic view of a wavefront direction mapping catheter system embodying the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference first to FIG. 1, therein is illustrated a wavefront direction mapping catheter system 10 embodying the principles of the present invention. As will be further described, the system 10 includes a cardiac wire catheter 12 which, when placed on the inner surface of the heart, identifies the direction of the electric field wavefront passing through the heart, and provides a signal via a computerized signal analysis arrangement, indicating the manner in which the catheter should be moved in order to push the tip of the catheter toward the source of the wavefront. The ability to move the catheter toward the wavefront greatly reduces the time needed to "electrically map" the heart for the site of earliest activation.

As will be described, the catheter 12 includes a bipolar electrode array at the distal tip portion thereof. Two wire ends or electrodes create a bipolar contact with the internal surface of the heart. As the cardiac electric field wavefront approaches the bipolar electrodes, a current is induced through the wire to a recording amplifier and computer of the analysis arrangement. The morphology of the recording identifies which pole of the electrode is affected by the approaching wavefront first. Because a single bipolar contact supplies only limited information about the source of the wavefront, the present invention preferably is configured to include first and second pairs of orthogonally arranged bipolar electrodes. By this arrangement, the second bipolar contact that is oriented perpendicular to the first bipolar contact provides the additional information needed to identify the exact wavefront angle of approach. Calculations of the size of the recordings from the two bipolar contacts are used to create vector information on the wavefront. This information is then translated to output control signals which identify the manner in which the position control mechanism of the system needs to be moved in order to move the catheter tip toward the source of the wavefront.

With further reference to the drawings, the present system 10 further includes a connector assembly 14 which includes wire leads from the bipolar electrodes of the catheter 12, as well as the necessary mechanical components for effecting three-dimensional movement of the catheter 12 including rotational movement of a distal tip portion of the catheter with respect to the catheter body. The connector assembly 14 is operatively connected with a computerized signal analyzer 16 which receives signals from the bipolar electrodes of the catheter in response to the wavefront passing over the catheter. The analyzer 16 then provides output signals indicating the manner in which the catheter needs to be translated in order to move the electrode array toward the source of the wavefront, with tissue ablation thereafter effected as necessary. A position controller 18 receives the output signals from signal analyzer 16, and includes suitable mechanical controls for selective positioning of the catheter 12.

Figure 2:
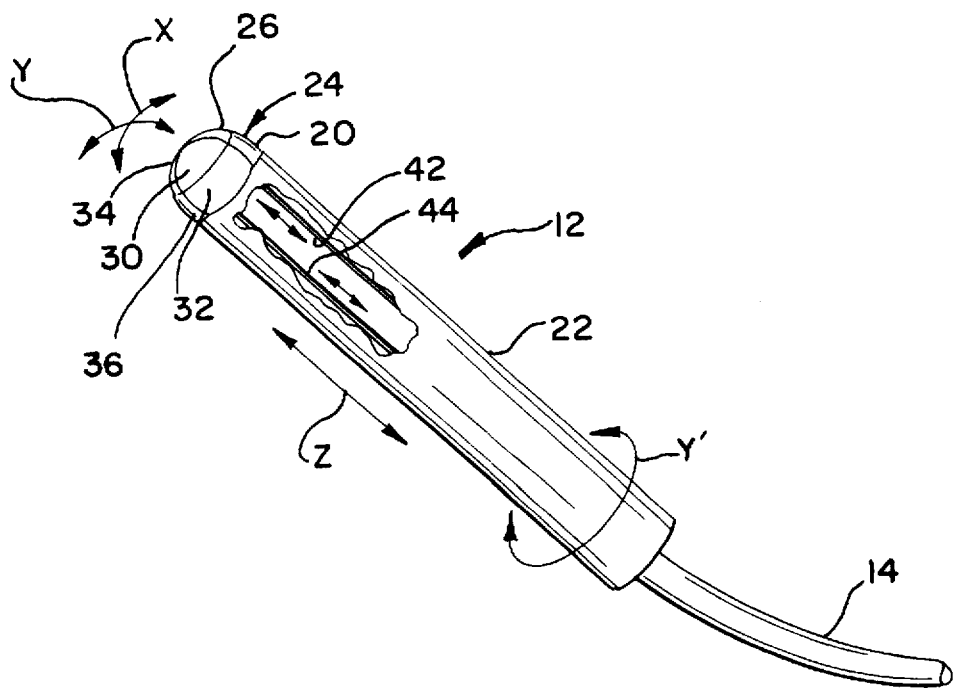
FIG. 2 is a perspective view, partially cut away, of the internally positionable catheter of the present system.
Figure 3:
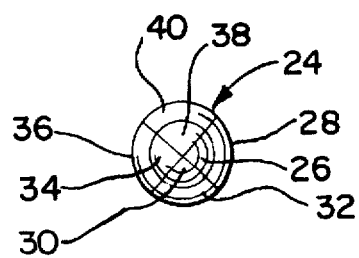
FIG. 3 is a top plan view of the catheter illustrated in FIG. 2.

With particular reference to FIG. 2, therein is further illustrated the catheter 12 of the present mapping system. The catheter 12 includes a generally elongated catheter body 22, which defines a longitudinal axis of the catheter, and a movably mounted catheter distal tip portion 24 positioned at the distal portion of catheter body 22. In accordance with the present invention, the distal tip portion 24 carries a bipolar electrode array, which preferably includes at least four (4) (i.e., first and second pairs), and most preferably eight (8) bipolar electrodes. As will be observed, the distal tip portion 24 of the catheter is generally spherically shaped, and in the preferred embodiment, includes a pair of axially spaced electrodes in each of the four quadrants of the generally spherically shaped distal tip portion. Thus, the distal tip portion includes axially spaced electrodes 26, 28, in a first quadrant, axially spaced electrodes 30, 32 in a second quadrant, axially spaced electrodes 34 and 36 in a third quadrant, and axially spaced electrodes 38, 40 in the fourth quadrant of the distal tip portion 24 of the catheter.

The configuration of the electrode array at the distal tip portion of the catheter is an important feature of the present invention. it is contemplated that by the illustrated configuration of the electrode array, four electrodes, configured as first and second perpendicular or orthogonal pairs of bipolar electrodes, will be in close proximity with the internal surface of the heart to supply accurate information about the direction of the source of the electrical wavefront. It is contemplated that distal tip portion 24 can touch the heart surface head-on, or on its side. Accordingly, the eight (8) electrodes of the array are arranged at the tip such that one of several different orientations of four electrodes can be chosen for mapping. A grouping of four electrodes positioned in orthogonally oriented pairs, is referred to as a diamond site. The diamond site that is in the best position with the heart surface is used to generate the directional information processed by signal analyzer 16 for providing output signals for operation of position controller 18. The configuration of the eight (8) electrodes at the generally spherical distal tip portion 24 allows for six (6) different diamond sites. It is contemplated that the best diamond site to be employed for signal processing be determined by one of several techniques, i.e., by determining via the signal analyzer 16 which site provides the largest signal amplitude, or the smallest stimulation threshold.

As noted, the catheter 12 of the present system is configured to permit selective positioning of distal tip portion 24 with respect to catheter body 22. To this end, the distal tip portion 24 is movably mounted on the catheter body 22 for relative rotational movement about a first axis (referred to as the "x-axis") denoted by rotational arrows "x" in FIG. 2. Rotational movement about this first axis can be effected by position controller 18 via connector assembly 14, such as by the provision of operating cables 42, 44 (FIG. 2) which extend from the connector assembly 14, through catheter body 22, and are operatively connected to the rotatably mounted distal tip portion 24. A suitable swivel, ball-and-socket joint, or other mechanical pivot arrangement, can be employed for suitable mounting of the distal tip portion 24.

The present invention contemplates that the distal tip portion 24 be further movable about a second rotational axis (the y-axis) perpendicular to the first x-axis of rotation. Rotation about this second axis can be effected by either: (1)

rotational movement of the distal tip portion with respect to the catheter body 22 about an axis perpendicular to both the first, x-axis and the longitudinal axis of the catheter, or (2) by rotational axis of the distal tip portion about the longitudinal axis defined by the catheter body 22, such as by rotation with the catheter body 22 as it is rotated or "torqued" about its longitudinal axis. Rotational movement of the distal tip portion with respect to the catheter body can be provided in a manner similar to the manner in which rotation about the x-axis is effected, such as through mechanical movement of the distal tip portion via cables or the like relative to the catheter body. Such rotational movement about the y-axis is denoted by the rotational arrow "y" of FIG. 2. Alternately, rotation about the second axis, perpendicular to the first y-axis and coaxial with the catheter axis, can be effected by rotation of the catheter 12 about its own longitudinal axis, as denoted by rotational arrows "y'" of FIG. 2. Either manner of rotation effects positioning of the distal tip portion about an axis perpendicular to the first x-axis, with the second axis of rotation being either perpendicular to the x-axis as well as the longitudinal axis of the catheter body, or perpendicular to the x-axis, and coaxial with the longitudinal axis of the catheter body.

Movement of the distal tip portion 24 of the catheter, and the bipolar electrode array mounted thereon, along a third axis, the z-axis, is effected by translation of the catheter along its longitudinal axis. This is denoted by displacement arrows "z" of FIG. 2.

With further reference to FIG. 1, processing of signals received from the electrode array of the distal tip portion of catheter 12 are processed by signal analyzer 16, generally in accordance with known techniques for processing and analyzing the electrical wavefront signal data. Such techniques are discussed in *Practical Electrocardiography*, Henry J. L. Mariott, M.D., seventh edition, 1983, and in U.S. Pat. No. 5,433,198, to Desai, hereby incorporated by reference. Signals from the first and second pairs of bipolar electrodes, which form the selected diamond site for signal analysis, are processed and analyzed via an x-axis bipolar signal processor 50, a y-axis bipolar signal processor 52, and a z-axis bipolar signal processor 54. Signal processing is integrated by a wavefront vector calculator 56, which in turn operates via vector processor 58 of the signal analyzer 16 to provide output signals for directing the catheter toward the source of the wavefront. The signal analyzer 16 may include a suitable display 60 for displaying vector calculations and related information regarding the processing of signals received from the electrode array.

The position controller 18 of the present system is illustrated in FIG. 1 in exemplary form, with the understanding that the specific configuration of the controller can be widely varied while keeping with the principles disclosed herein. In essence, the signal analyzer 16 of the present system includes an indicator arrangement, which may be provided and mounted on the controller 18 itself, to provide a visual indication of the manner in which the controller is to be operated for positioning the distal tip portion 24 of catheter 12 in the direction of the wavefront. In the illustrated embodiment, the controller 18 includes an x-axis control lever 64, and a y-axis control lever 66 for respectively positioning the catheter distal tip portion 24 with respect to the first and second rotational axes, i.e., the x-axis and the y-axis. The indicator arrangement of the signal analyzer can be provided in a form such as illustrated, including indicator lights 68, 70 for indicating the direction in which the x-axis lever 64 is to be moved, and similarly, indicator lights 72, 74 for indicating the direction in which the y-axis lever 66 is to be moved for effecting movement of the distal tip portion 24 in the direction of the wavefront. Indication of the manner in which the controller is to be operated for effecting z-axis movement is also contemplated, such as by coordinated operation of light 68, 72 with each other, 70, 74 with each other, or by some other suitable indicator arrangement.

The illustrated configuration of the controller 84 is exemplary. Dual lever arrangements, joy stick-control arrangements, and other suitable mechanisms are well-known in the medical instrument arts for effecting the desired selective positioning of the catheter 12 in accordance with the present invention. While the use of indicators 68, 70 and 72, 74 is illustrated for showing the manner in which lever 64, 66 are to be operated, such illustration is intended as exemplary, with the understanding that series of indicator lights (such as for indicating direction and extent of motion), pictographs, LCD or LED read outs, or other suitable indicating arrangements can be employed for providing the desired visual indication in response to the output signals of signal analyzer 16 so that the operator can effect operation of position controller 18 in the manner required for moving the distal tip portion of catheter 12 in the direction of the source of the wavefront. Such indicating arrangements can be provided on the controller 18, or otherwise provided such as via monitors or the like typically employed during use of such a catheter system.

Thus, the present system can be operated to determine the locus of wavefront generation by positioning catheter 12 so that the bipolar electrode array carried thereby is in electrical contact with the heart, with analysis of the signals from the array permitting the tip portion to be moved in response to the signals toward the source of the wavefront. By repeating the signal analysis and moving steps, the bipolar electrode array can be positioned at the source of the wavefront or within the wavefront circuit.

While mapping of wavefronts is efficiently and accurately achieved through use of the present invention, it is contemplated that the present system be further configured for effecting tissue ablation, thus obviating the need for removal of the catheter 12, and reinsertion of an ablating device. Ablation is effected such as by radio frequency energization of one or more selected bipolar electrodes of the bipolar electrode array mounted on distal tip portion 24 of catheter 12. Techniques for effecting tissue ablation are well-known, such as discussed in U.S. Pat. No. 5,383,917, to Desai et al., hereby incorporated by reference.

Use of the present system significantly enhances the efficiency of wavefront mapping, and ablation of important life threatening arrhythmias. Prior to development of the present invention, on average, five (5) to six (6) hours are required to complete an electrophysiologic study with radio frequency ablation of re-entrant tachycardia. A significant percentage of this time is directly due to the time involved in electrically mapping the heart to identify the site of earliest activation.

By use of a computerized signal analyzer 16, highly versatile use of the present system is achieved. As noted, the signal analyzer is operated to determine which two othogonally arranged pairs of the bipolar electrode array are best suited for providing the desired signals for vector analysis of the electrical wavefront. The analyzer can further be operated so that the point of the wavefront morphology upon which signal analysis is effected can be variably selected, facilitating discrimination of different aspects of different arrhythmias. Computerization of the signal analyzer 16 permits the present system to be operated in a wide variety of different fashions, thus permitting versatile use of the present system for applications other than those specifically disclosed herein.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover, by the appended claims, all such modifications as fall within the scope of the claims.

What is claimed is:

1. A wavefront direction mapping catheter system, comprising:

a catheter configured for positioning internally of a patient's heart, said catheter including a generally elongated catheter body defining a longitudinal axis, and a distal tip portion movably mounted on a distal end of said catheter body, said tip portion including a bipolar electrode array including first and second pairs of orthogonally positioned bipolar electrodes for contact with the patient's heart for providing signals in response to a wavefront moving through the heart;

electrically conductive connector means joined to said bipolar electrode array, and extending from said patient for providing signals from said bipolar electrode array;

signal analysis means for analyzing signals received from said electrode array via said connector means, said analysis means being configured to analyze the direction of said wavefront, and provide an output signal for directing said catheter toward the source of said wavefront; and position control means operatively connected to said catheter for selectively positioning said distal tip portion relative to said catheter body about a rotational axis in response to said output signal of said signal analysis means for mapping the direction of the wavefront.

2. A wavefront direction mapping catheter system in accordance with claim 1, including ablation means operatively connected to said electrode array for effecting arrhythmia ablation.

3. A wavefront direction mapping catheter system in accordance with claim 1, wherein said catheter distal tip portion has a generally spherical shape, with said electrodes of said first and second pairs of electrodes of said array being respectively positioned in quadrants of said generally spherically shaped distal tip portion.

4. A wavefront direction mapping catheter system in accordance with claim 1, wherein said catheter distal tip portion is generally spherically shaped, said bipolar electrode array comprising a pair of axially spaced electrodes positioned in each quadrant of said generally spherically shaped distal tip portion.

5. A wavefront direction mapping catheter system in accordance with claim 1, wherein said rotational axis about which said distal tip portion is positionable comprises a first rotational axis, said position control means further including means for selectively positioning said distal tip portion about a second rotational axis perpendicular to said first rotational axis.

6. A wavefront direction mapping catheter system in accordance with claim 6, including means for positioning said distal tip portion about said second rotational axis perpendicular to said longitudinal axis of said catheter body.

7. A wavefront direction mapping catheter system in accordance with claim 5, including means for positioning said distal tip portion said second rotational axis coaxially with said longitudinal axis of said catheter body.

8. A wavefront direction mapping catheter system in accordance with claim 5, wherein signal analysis means includes indicator means for providing a visual indication of the manner in said position control means is to be operated for positioning said distal tip portion of said catheter in the direction of said wavefront.

9. A wavefront direction mapping catheter system in accordance with claim 8, wherein said position control means includes means to move said catheter axially of the longitudinal axis of said catheter body, said indicator means being configured to provide a visual indication that said control means is to be operated to move said catheter axially of said longitudinal axis for positioning said distal tip portion in the direction of said wavefront.

10. A method of mapping the wavefront direction of a patient's heart, comprising the steps of:

providing a catheter having a body portion defining a longitudinal axis, and a distal tip portion movably mounted on a distal end of said catheter body and including a bipolar electrode array having first and second pairs of orthogonally positioned bipolar electrodes for providing signals in response to a wavefront moving through the heart;

positioning said catheter internally of the heart so that said bipolar electrode array is in electrical contact with the heart;

analyzing the signals from said bipolar electrode array for analyzing the direction of the wavefront, and for providing an output signal for directing said catheter toward the source of the wavefront; and selectively rotationally positioning the distal tip portion of said catheter relative to said catheter body in response to said output signal for mapping the direction of the wavefront.

11. A method of mapping wavefront direction in accordance with claim 10, wherein said step of relatively rotationally positioning said distal tip portion includes rotationally positioning said distal tip portion about first and second axes which are perpendicular to each other.

12. A method of determining the locus or circuit of wavefront generation of a patient's heart, comprising the steps of:

providing a catheter having a body portion defining a longitudinal axis, and a distal tip portion movably mounted on a distal end of said catheter body and including a bipolar electrode array having at least one pair of bipolar electrodes for providing signals in response to a wavefront moving through the heart;

positioning said catheter internally of the heart so that said bipolar electrode array is in electrical contact with the heart;

analyzing the signals from said bipolar electrode array for analyzing the direction of the wavefront, and for providing an output signal for directing said catheter toward the source of the wavefront; and moving the distal tip portion of said catheter in response to said output signal toward the source; and repeating said analyzing and moving steps until said bipolar electrode array on said distal tip portion is positioned at the source of the wavefront or within the wavefront circuit.

13. A method of determining the locus of wavefront generation in accordance with claim 12, wherein said step of moving said distal tip portion includes rotationally positioning said distal tip portion about first and second axes which are perpendicular to each other.

14. A method of mapping wavefront direction in accordance with claim 12, including providing said bipolar electrode array with first and second pairs of orthogonally positioned bipolar electrodes.

15. A method of mapping wavefront direction in accordance with claim 12, including ablating tissue in the heart by energization of said bipolar electrode array.

16. A method of mapping the wavefront direction of a patient's heart, comprising the steps of:

providing a catheter having a body portion defining a longitudinal axis, and a distal tip portion movably mounted on a distal end of said catheter body and including a bipolar electrode array having at least one pair of bipolar electrodes for providing signals in response to a wavefront moving through the heart;

positioning said catheter internally of the heart so that said bipolar electrode array is in electrical contact with the heart;

analyzing the signals from said bipolar electrode array for analyzing the direction of the wavefront, and for providing an output signal for selectively directing said catheter toward the source of the wavefront;

selectively rotationally positioning the distal tip portion of said catheter relative to said catheter body in response to the said output signal for mapping the direction of the wavefront; and ablating tissue in the heart by energization of the bipolar electrode ray.

* * * * *